United States Patent [19]

Finnieston

[11] 4,417,570
[45] Nov. 29, 1983

[54] LOWER ARM BRACE

[76] Inventor: Alan Finnieston, 2480 W. 82 St., Hialeah, Fla. 33016

[21] Appl. No.: 330,801

[22] Filed: Dec. 15, 1981

[51] Int. Cl.³ .................................................. A61F 5/04
[52] U.S. Cl. ................................................. 128/87 R
[58] Field of Search ..................... 128/87 R, 77, 89 R, 128/90, 165; 2/16, 18, 19, 20

[56] References Cited

U.S. PATENT DOCUMENTS

| | | | |
|---|---|---|---|
| 2,682,869 | 7/1954 | Papp | 128/87 R |
| 3,701,349 | 10/1972 | Larson | 128/89 R |
| 3,911,497 | 10/1975 | Lewis, Jr. et al. | 128/89 R |
| 4,190,902 | 3/1980 | Rhee | 128/87 R |
| 4,241,922 | 12/1980 | Elliott, Jr. | 128/87 R |

OTHER PUBLICATIONS

Clinical Orthopaedics, Jan. Feb. 1980, vol. 146, pp. 175-183, "Functional Bracing of Colles' Fractures".

Primary Examiner—John D. Yasko
Attorney, Agent, or Firm—Larson and Taylor

[57] ABSTRACT

A lower arm brace to be secured about the lower arm of a wearer and including an inner segment and an outer segment sized for intermating nesting relationship of the inner segment with respect to the outer segment for clam shell type engagement of the segments about the arm of a wearer to lend support to it and wherein a plurality of straps may be provided to maintain the two in relation with another about the arm of a wearer.

5 Claims, 6 Drawing Figures

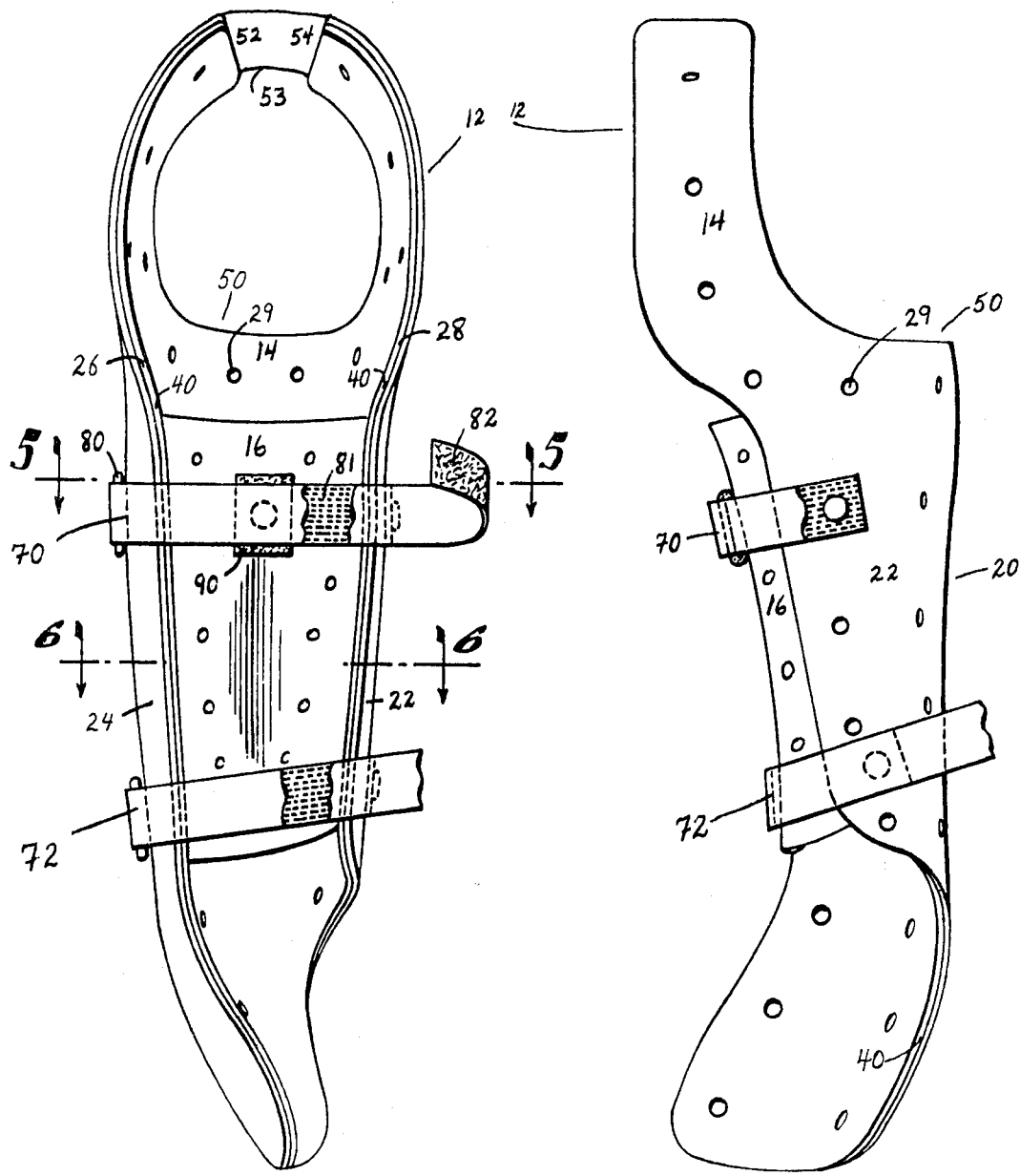

LOWER ARM BRACE

FIELD OF THE INVENTION

This invention relates to a lower arm brace.

BACKGROUND OF THE INVENTION

In the past there have been numerous types of devices which have been utilized for persons having an injured or broken arm such as the well-known plaster cast. This invention is of a lower arm brace which is adapted to be secured about the arm of a wearer and wherein a first and a second or, rather, an outer and an inner segment are provided for clamping or clam shell type interengagement with one another about the arm of a wearer to apply pressure to the flesh so as to support the lower arm bone. The device includes an adjustable means to adjust the amount of pressure which is applied by the two segments when in nested relation with one another and about the arm of a wearer.

OBJECTS OF THE INVENTION

It is a general object of this invention to provide a lower arm brace comprising an outer segment and an inner segment which intermate with one another and which are maintained in position by keeper means which may be in the form of a strap preferably of Velcro secured to the outer segment.

It is another object of this invention to provide a lower arm brace of the type set forth wherein the base of the U-shaped outer segment is provided with a contoured surface to apply pressure to the flesh in the outer side of the lower arm of a wearer to exert a stabilizing support to a lower arm about which the brace is secured.

It is another object of this invention to provide a brace of the type described wherein a plurality of perforations are provided in an outer segment to accommodate breathing and use of the device.

It is another object of this invention to provide a device of the type described wherein a liner means is provided along the outer segment to provide a padding along the relatively tender lower arm bones, wrist and knuckles of a user and preferably wherein there is an adjustment means provided to adjust the force exerted by these segments when in telescoping relation with one another, that is, with the inner segment received within the outer segment and in tight clamping relation about the arm of a wearer.

It is another object of this invention to provide a lower arm brace of the type set forth wherein the base of the U-shaped outer segment is extended beyond the wrist and curved inward with a contoured surface to apply pressure to the flesh in the outer side of the hand of a wearer to exert a stabilizing support to the hand in relation to the lower arm bones about which the brace is secured.

In accordance with these and other objects which will become apparent hereinafter, the instant invention will now be described with reference to the accompanying drawings in which:

DESCRIPTION OF THE DRAWINGS

FIG. 1 is a front elevation view of the lower arm brace;

FIG. 2 is a side elevation view of the inner portion of the lower arm brace;

DESCRIPTION OF THE PREFERRED EMBODIMENT

Figure 3:
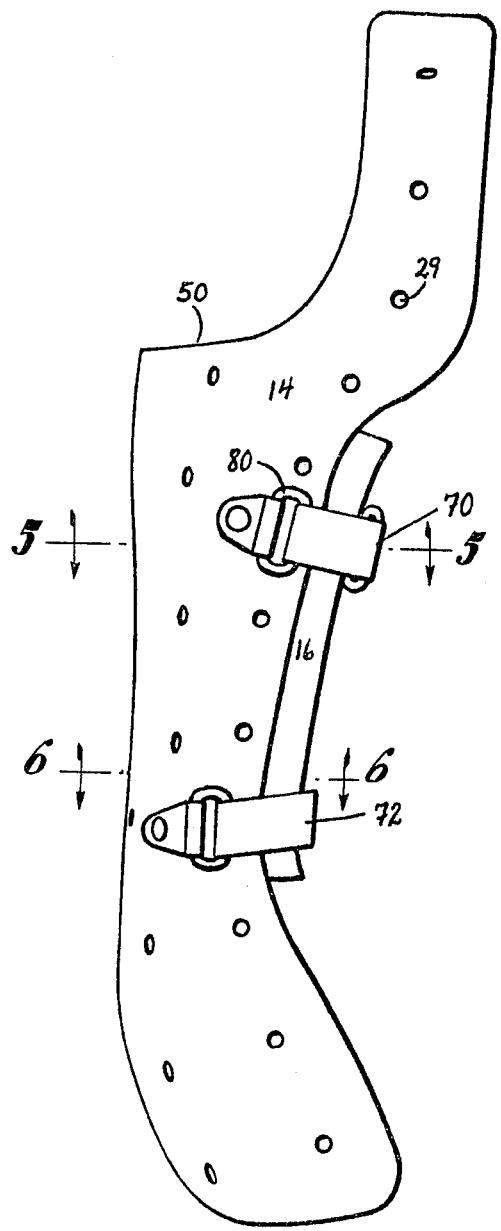
FIG. 3 is a side elevation view of the outer portion of the lower arm brace.
Figure 4:
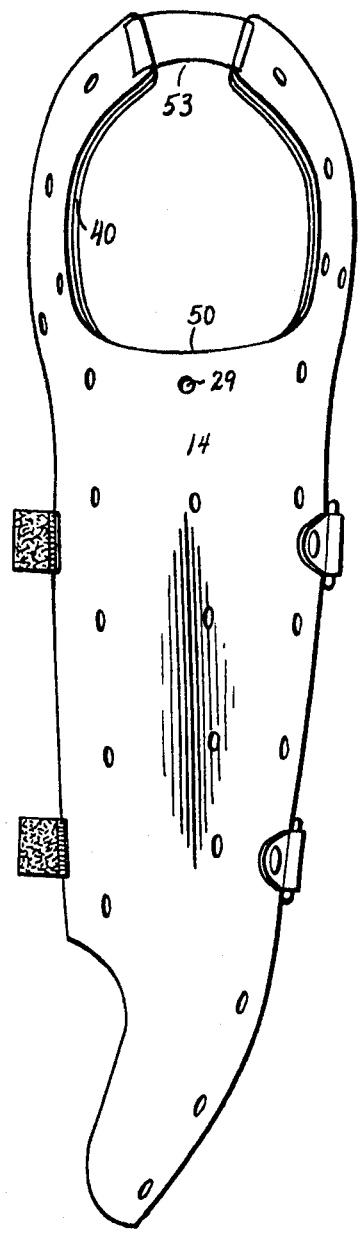
FIG. 4 is a rear elevation view of the lower arm brace.

Referring to the drawings wherein like reference characters designate like or corresponding parts throughout the several views and referring particularly to the lower arm brace generally designated by the numeral 12. It is composed of an outer segment 14 and an inner segment 16 which are intermated into clam shell relation, so that one is slidable with respect to the other, i.e., expandable in a horizontal direction, generally as seen in FIGS. 5 and 6 to accommodate larger and smaller girths of arms so that one size generally fits all.

Figure 5:
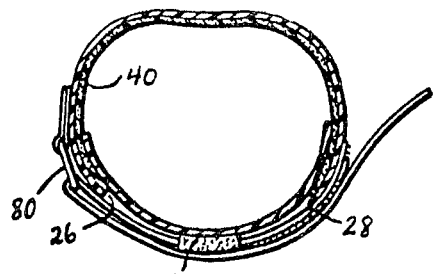
FIG. 5 is a view in cross section taken on the plane indicated by the line 5—5 of the lower arm brace.
Figure 6:
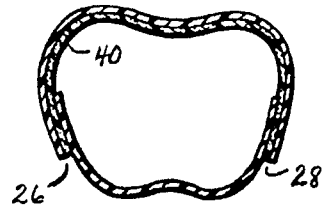
FIG. 6 is a view in cross section taken on the plane indicated by the line 6—6 of the lower arm brace.

Generally speaking, the outer segment is U-shaped in cross section, see FIGS. 5 and 6, and of a length of about 20 inches. The base 20 of the outer portion is generally contoured to the shape of the lower arm which has been held so that the palm of the hand is facing inward towards the body and the side walls 22 and 24 are curved smoothly and fairly to spaced terminal ends as at 26 and 28 which are spaced from one another. The material is of plastic within the rigid range and is in a flexible relatively thin construction so that the mouth between the terminal ends 26 and 28 can be flexed or expanded by hinged movement of the side walls relative to the base. This segment 14 is perforated as indicated by the holes of which 29 is representative, and which are arranged in a pattern throughout the outer segment. The outer segment has an outside surface and an inside surface. The inside surface is lined with foam material as is generally designated by the numeral 40. As best seen in FIGS. 1 through 4, the upper edge 50 is somewhat larger than the lower or bottom end so that the braces somewhat taper to conform to the arm of a wearer. Preferably the liner is of foam material and beveled slightly.

The mating interior segment is generally designated by the numeral 16; and it is seen that it is generally U-shaped but somewhat rounded or curved as is best shown in FIGS. 3, 5 and 6. As shown in FIGS. 5 and 6, the upper edge is somewhat larger than the lower or bottom end so that the brace is somewhat tapered to conform to the lower arm of a wearer. This segment is also of rigid plastic material in a flexible construction.

In use, the inner segment fits over the lower arm bones of a wearer while the base of the outer section overlays the flesh along the outer portion of a wearer's arm. As seen in FIGS. 1 through 5, keeper means are provided which may be of a plurality of straps such as 70 and 72. One end of each of the straps is adapted to be received in a buckle, such as 80, fixed along and adjacent one of the mouth edges. The other end of these straps are secured to the opposite edge 28 by suitable means such as that shown and preferably these straps are of Velcro, each with a portion adjacent one end which comprises J-hooks and another portion which comprises loops to intermate with the J-hooks providing an adjustable strap, as indicated by the numerals 81 and 82.

In any event, once arranged about the arm of a wearer, the straps are tightened. Preferably, the inner segment includes at least a single loop, such as that designated by the numeral 90, which serves to maintain the outer segment and the inner segment in generally mating relation, resisting relative vertical displacement of the two segments when in position on the arm of a wearer. As shown in FIGS. 1 through 3, the interior segment is substantially smaller than the outer segment. The contours of the inner segment as shown in FIG. 6 operate to separate the two bones of the lower arm. The inner member additionally is perforated to allow for breathing of the skin.

To maintain the proper location of the device, a strap is located to connect the end parts of the outer portion at the end points 52 and 54 which surrounds the area above the elbow around the upper arm. In the preferred embodiment, the base 20 is cutaway at the upper portion of the outer segment to facilitate the location and movement of the elbow.

While this invention has been shown and described in what is considered to be a practical and preferred embodiment, it is recognized that departures may be made within the spirit and scope of this invention which is, therefore, not to be limited except as set forth in the claims which follow within the doctrine of equivalence.

What is claimed is:

1. A lower arm brace comprising an elongate, outer member, having a base portion and curved side walls to form a generally U-shaped cross section,
    one end of the base portion being extended to form a wrist extension being angled with respect to the base portion so as to maintain the hand of the wearer at an angle with respect to the forearm, the hand being turned inwardly towards the body of the wearer,
    the other end of the base portion extending to a point adjacent the elbow of the wearer said other end of the base having extensions on the side walls which project above the lateral side edges of the side walls, and curve inwardly towards each other, said extensions being of a reduced width so as to partially surround the upper arm above the elbow without surrounding the elbow with the ends of said extensions being in closely spaced relation, said extensions being flexible to fit various sized upper arms and serving to prevent the brace from sliding with respect to a predetermined position on the arm,
    an inner member having a base portion and curved side walls to form a generally U-shaped cross section,
    said inner and outer members interfitting to be positioned in embracing relation of the inner and outer surface of the lower arm between the elbow and wrist and
    means to hold the members releasably and adjustably about the lower arm in clamping sleeve-like relation.

2. A lower arm brace according to claim 1 wherein the wrist extension covers the back of the hand of the wearer to a point adjacent the second knuckle without severely retarding the usage of the palm and fingers.

3. A lower arm brace according to claim 1 wherein said inner and outer members comprise molded plastic structures within the rigid range.

4. A lower arm brace according to claim 1 wherein said means to hold the members releasably comprises velcro fastener straps and each of said members has a plurality of holes therethrough arranged in a venting pattern.

5. A lower arm brace according to claim 1 wherein the extensions on the base portion surrounding the area above the elbow are interconnected by a strap.

* * * * *

UNITED STATES PATENT AND TRADEMARK OFFICE
CERTIFICATE OF CORRECTION

PATENT NO. : 4,417,570

DATED : November 29, 1983

INVENTOR(S) : Alan Finnieston et al.

It is certified that error appears in the above-identified patent and that said Letters Patent is hereby corrected as shown below:

On the title page item [76] insert:

-- Joseph B. Zagorski
440 Castania
Coral Gables, Fla. 33134 --.

Signed and Sealed this

Twenty-eighth Day of February 1984

[SEAL]

Attest:

GERALD J. MOSSINGHOFF

Attesting Officer     Commissioner of Patents and Trademarks